(12) United States Patent
Tuschel et al.

(10) Patent No.: US 7,268,330 B2
(45) Date of Patent: *Sep. 11, 2007

(54) APPARATUS AND METHOD FOR DEFINING ILLUMINATION PARAMETERS OF A SAMPLE

(75) Inventors: David Tuschel, Monroeville, PA (US); Thomas Voigt, Export, PA (US); Chenhui Wang, Stow, OH (US)

(73) Assignee: Chemimage Corporation, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/451,621

(22) Filed: Jun. 13, 2006

(65) Prior Publication Data

US 2007/0007444 A1 Jan. 11, 2007

Related U.S. Application Data

(63) Continuation of application No. 11/045,081, filed on Jan. 31, 2005, now Pat. No. 7,060,955.

(51) Int. Cl.
*G01J 1/32* (2006.01)
(52) U.S. Cl. .............................. 250/205; 250/226
(58) Field of Classification Search ............... 250/205, 250/208.1, 216, 226
See application file for complete search history.

(56) References Cited

U.S. PATENT DOCUMENTS

| | | | |
|---|---|---|---|
| 5,194,912 A | 3/1993 | Batchelder et al. | |
| 5,377,003 A | 12/1994 | Lewis et al. | |
| 5,377,004 A | 12/1994 | Owen et al. | |
| 5,394,499 A | 2/1995 | Ono et al. | |
| 5,442,438 A | 8/1995 | Batchelder et al. | |
| 5,493,443 A | 2/1996 | Simon et al. | |
| 5,528,393 A | 6/1996 | Sharp et al. | |
| 5,623,342 A | 4/1997 | Baldwin et al. | |
| 5,689,333 A | 11/1997 | Batchelder et al. | |
| 5,710,626 A | 1/1998 | O'Rourke et al. | |
| 5,784,162 A | 7/1998 | Cabib et al. | |
| 5,862,273 A | 1/1999 | Pelletier | |
| 5,866,430 A | 2/1999 | Grow | |
| 5,901,261 A | 5/1999 | Wach | |
| 5,911,017 A | 6/1999 | Wach et al. | |
| 5,943,122 A | 8/1999 | Holmes | |
| 5,974,211 A | 10/1999 | Slater | |

(Continued)

FOREIGN PATENT DOCUMENTS

WO  WO95 11624  5/1995

OTHER PUBLICATIONS

Morris, Hoyt, and Treado, "Imaging Spectrometers for Fluorescence and Raman Microscopy: Acousto-Optic and Liquid Crystal Tunable Filter," Applied Spectroscopy, vol. 48, No. 7, 1994.

(Continued)

*Primary Examiner*—Que T. Le
(74) *Attorney, Agent, or Firm*—Daune Morris, LLP

(57) ABSTRACT

In one embodiment, the disclosure relates to a method for determining illumination parameters for a sample, the method may include obtaining an absorption band of the sample; obtaining an emission band of the sample and determining the illumination parameters for the sample as a function of the absorption band and the emission band of the sample.

17 Claims, 1 Drawing Sheet

U.S. PATENT DOCUMENTS

| | | |
|---|---|---|
| 6,002,476 A | 12/1999 | Treado |
| 6,006,001 A | 12/1999 | Alfano et al. |
| 6,088,100 A | 7/2000 | Brenan et al. |
| 6,091,872 A | 7/2000 | Katoot |
| 6,222,970 B1 | 4/2001 | Wach et al. |
| 6,483,641 B1 | 11/2002 | MacAulay |
| 6,485,413 B1 | 11/2002 | Boppart et al. |
| 6,571,117 B1 | 5/2003 | Marbach |
| 6,697,665 B1 | 2/2004 | Rava et al. |
| 6,891,613 B2 * | 5/2005 | Wolleschensky et al. ... 356/326 |

OTHER PUBLICATIONS

Morris, Hoyt, Miller and Treado, "Liquid Crystal Tunable Filter Raman Chemical Imaging," Applied Spectroscopy, No. 50, No. 6, Jun. 1996.

Skinner, Cooney, Sharma and Angel, "Remote Raman Microimaging Using an AOTF and a Spatially Coherent Microfiber Optical Probe," Applied Spectroscopy, vol. 50, No. 8, 1996.

* cited by examiner

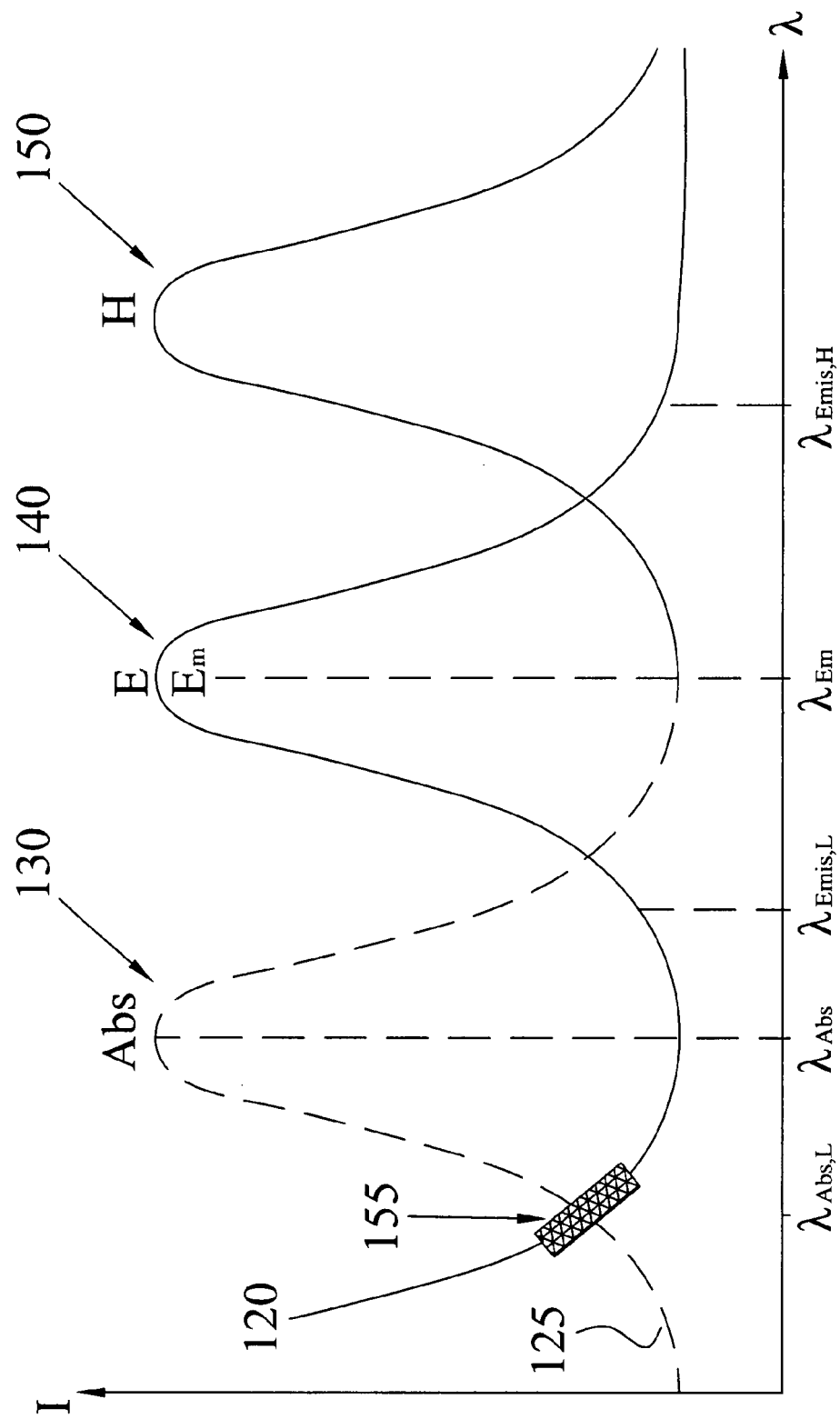

APPARATUS AND METHOD FOR DEFINING ILLUMINATION PARAMETERS OF A SAMPLE

The instant application claims priority benefit in continuation of application Ser. No. 11/045,081 now U.S. Pat. No. 7,060,955 filed Jan. 31, 2005 by the inventors herein, the entirety of which is incorporated herein by reference.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscopes or rigid borescopes can be employed. For very large scale objects, such as planetary objects, telescopes are appropriate image gathering optics.

Regardless of the type of optical equipment, a first step in any spectroscopic investigation is defining a suitable wavelength for illuminating the sample. The step of defining an suitable wavelength for illuminating the sample becomes even more important when simultaneous multiple images of the sample are sought. Conventional methods suggest illuminating a sample with a first wavelengths (e.g., NIR or VIS) to obtain a first image, followed by illuminating the sample with a second wavelengths to obtain a second image (e.g., Raman or dispersive Raman) to obtain a second image. Consequently, the conventional process are time consuming and are not suited for simultaneous imaging of the ample. There is a need for a apparatus and method for determining illumination parameters of a sample a priori of illuminating the sample.

SUMMARY OF THE DISCLOSURE

In one embodiment, the disclosure relates to a method for determining illumination parameters for a sample, the method including obtaining an absorption band of the sample; obtaining an emission band of the sample; and determining the illumination parameters for the sample as a function of the absorption band and the emission band of the sample.

In another embodiment, the disclosure relates to a system for defining illumination parameter for a sample comprising an illumination source, an optical train and a processor programmed with instructions for obtaining an absorption band of the sample; obtaining an emission band of the sample, the emission band including a lower wavelength range and an upper wavelength range; and determining the illumination parameters for the sample as a function of the absorption band and the emission band of the sample.

In still another embodiment, the disclosure relates to a method for determining illumination parameters for a sample, the method comprising simultaneously illuminating the sample with illuminating photons, the illuminating photons defining a first wavelength and a second wavelength; obtaining at least one of an emission band and an absorption band of the sample from the illuminating photons interacting with the sample, the emission band defining a lower wavelength range and an upper wavelength range; and determining the illumination parameters for the sample as a function of the absorption band and the emission band of the sample.

Still another embodiment of the disclosure relates to a system for defining illumination parameter for a sample comprising an illumination source, an optical train and a processor programmed with instructions to simultaneously illuminate the sample with illuminating photons, the illuminating photons defining a first wavelength and a second wavelength; obtain at least one of emission band and an absorption band of the sample from the illuminating photons interacting with the sample, the emission band defining a lower wavelength range and an upper wavelength range; and determine the illumination parameters for the sample as a function of the absorption band and the emission band of the sample.

BRIEF DESCRIPTION OF THE DRAWING

The FIGURE graphically illustrates the relationship between intensity and wavelength of a sample.

DETAILED DESCRIPTION

The disclosure generally relates to a method and apparatus for determining illumination parameters for a sample. Having an a priory knowledge of an optimal illumination wavelength for obtaining spectral images of a sample is particularly important in that the appropriate wavelength enable simultaneous imaging of the sample at several wavelengths. In one embodiment, the disclosure generally relates to a method and apparatus for determining illumination parameters for a sample. The illumination parameters enable, among others, simultaneous signal detection from the sample. The detection mode can be selected from the group consisting of wide field, Raman chemical imaging, multipoint, dispersive single point and dispersive line. The method and apparatus for obtaining simultaneous multimode images from a sample is discussed extensively in the co-pending patent application Ser. No. 11/045,051 filed concurrently by the co-inventors named herein, the specification of which is incorporated herein for background information.

The FIGURE graphically illustrates the relationship between intensity and wavelength of a sample. The method of obtaining absorption and emissivity bands are conventionally known. It is also known that emissive energy is associated with fluorescent imaging and absorption energy is associates with NIR. Thus, as a first step the sample is illuminated with photons of different frequencies. The illuminating photons (interchangeably, the detection photons) can include photons having wavelengths in the emission band and photons have wavelengths in the absorption band. Moreover, the sample may be illuminated with photons in a mode selected from the group including wide field, Raman chemical imaging, multipoint, single point and line illumination.

Referring again to the FIGURE, line 125 represents the energy absorption relationship of a sample exposed to emissive and absorption bands. Peak 130 represents the optimal intensity corresponding to absorption wavelength ($\lambda_{abs\text{-}opt.}$) 125. The absorption energy band is considered to extend from a low frequency wavelength ($\lambda_{abs\text{-}L}$) to a high frequency wavelength ($\lambda_{abs\text{-}H}$). In the FIGURE, line 120 illustrates the relation between the intensity and wavelength of absorption energy of the sample. Peak 140 represents the emissive intensity peak ($E_m$) having wavelength $\lambda_{Em}$. As with the absorption band, the emissivity intensity also defines a bandwidth limited by lower and upper wavelengths identified as ($\lambda_{Emis\_L}$) and ($\lambda_{Emis\_H}$), respectively.

According to one embodiment of the disclosure an optimal wavelength for Raman spectroscopic imaging occurs at a wavelength just below or about the low frequency range ($\lambda_{abs\text{-}low}$) of the absorption band. One embodiment of the disclosure relates to a method for defining illumination parameters for a sample by: (i) obtaining an absorption band of the sample; (ii) obtaining an emission band of the sample, the emission band having a lower wavelength range ($\lambda_{abs\text{-}low}$) and an upper wavelength range ($\lambda_{abs\text{-}high}$); and (iii) assessing the illumination parameters for the sample as a function of the absorption band and the emission band, and more specifically, as a function of the low frequency wavelength ($\lambda_{abs\text{-}low}$) of the sample. These steps cane be implemented sequentially or simultaneously. By way of example, this region is shown as 155 in the FIGURE. Thus, illumination parameter for the sample can be selected such that the parameters define a wavelength shorter than the wavelength of a peak in the emission spectrum. The illumination parameters may also be used to define a laser line or a suitable Raman wavelength.

In another embodiment, the optimal wavelength range for Raman can be found at about the region where the absorption bandwidth 130 and the Emission bandwidth intersect.

In the FIGURE, peak 150 represents Raman spectrum. Peak 1740 shows the peak of the emission spectrum and peak 130 shows the peak of the absorption spectrum.

While the steps of obtaining absorption band and emission band can be implemented sequentially, one embodiment of the disclosure relates to implementing both steps substantially simultaneously. In this manner, a multi-mode image of a sample can be obtained substantially simultaneously.

Thus, according to one embodiment of the disclosure a method for determining illumination parameters for a sample includes: simultaneously illuminating the sample with illuminating photons. The illuminating photons can have several different wavelengths or define a broad range of wavelengths. Next, the wavelengths for the emission band and the absorption bands of the sample can be defined. In addition, the emission band and the absorption band can define the wavelength for the peak intensity in each band as well as the lower and the upper wavelength ranges for each band. Using the lower wavelength of the absorption band ($\lambda_{abs\text{-}L}$) an optimal Raman wavelength detection wavelength for the sample can be defined as Raman scattered photons having wavelength about or below $\lambda_{abs\text{-}L}$. By way of example, one such region is shown as region 155 in the FIGURE. The illumination parameters thus obtained can be used to illuminate the sample with illuminating photons of different wavelengths to obtain simultaneous spectral images of the sample. The illuminating photons can be a laser line, wide-field, Raman chemical imaging, multipoint imaging, dispersive single point and dispersive lines specifically devised to be within the desired wavelength range.

In a system according to one embodiment of the disclosure, the illumination parameter for a sample includes one or more illumination sources, an optical train and a processor programmed with instructions to simultaneously illuminate the sample with illuminating photons and detect an emission band and an absorption band of the sample. The instructions can also include defining a lower wavelength range and an upper wavelength range for the band and determine the illumination parameters for the sample as a function of the absorption and the emission bands of the sample. Finally, the instructions may include defining a suitable Raman wavelength for the sample at a wavelength shorter than the lower wavelength range of the emission spectrum.

While the principles of the disclosure have been disclosed in relation to specific exemplary embodiments, it is noted that the principles of the invention are not limited thereto and include all modification and variation to the specific embodiments disclosed herein.

What is claimed is:

1. A method for determining an illumination parameter for a sample, the method comprising:
   obtaining an absorption band of the sample;
   obtaining an emission band of the sample; and
   determining the illumination parameter for the sample as a function of the absorption band and the emission band of the sample.

2. The method of claim 1, wherein the step of obtaining an absorption band of the sample further comprises the step of illuminating the sample.

3. The method of claim 1, wherein a suitable Raman wavelength occurs at a shorter wavelength defined by the emission band of the sample.

4. The method of claim 1, wherein the illumination parameter defines a laser line.

5. The method of claim 1, further comprising the step of illuminating the sample with photons in a mode selected from the group consisting of wide field, Raman chemical imaging, multipoint, single point and line illumination.

6. The method of claim 1, wherein the steps of obtaining an absorption band and obtaining an emission band are implemented simultaneously.

7. The method of claim 1, wherein the steps of obtaining an absorption band and obtaining an emission band are implemented sequentially.

8. A system for defining illumination parameters for a sample comprising an illumination source, an optical train and a processor programmed with instructions for
   obtaining an absorption band of the sample;
   obtaining an emission band of the sample, the emission band including a lower wavelength range and an upper wavelength range; and
   determining the illumination parameters for the sample as a function of the absorption band and the emission band of the sample.

9. The system of claim 8, wherein the step of obtaining an absorption band of the sample further comprises illuminating the sample.

10. The system of claim 8, wherein the illumination parameters define a wavelength below the lower wavelength range of the sample.

11. The system of claim 8, wherein a suitable Raman wavelength occurs at a wavelength below the lower wavelength range of the sample.

12. The system of claim 8, further comprising the step of illuminating the sample with photons in a mode selected from the group consisting of wide field, Raman chemical imaging, multipoint, single point and line illumination.

13. A method for determining illumination parameters for a sample, the method comprising:
   simultaneously illuminating the sample with illuminating photons, the illuminating photons defining a first wavelength and a second wavelength;
   obtaining at least one of an emission band and an absorption band of the sample from the illuminating photons interacting with the sample, the emission band defining a lower wavelength range and an upper wavelength range; and determining the illumination parameters for the sample as a function of the absorption band and the emission band of the sample.

14. The method of claim 13, further comprising illuminating the sample with photons having wavelength within the illumination parameters.

15. The method of claim 13, wherein the step of obtaining an absorption band of the sample further comprises illuminating the sample.

16. The method of claim 13, wherein a suitable Raman wavelength occurs at a wavelength shorter than the emission band.

17. The method of claim 13, wherein the step of illuminating the sample includes illuminating the sample with photons in a mode selected from the group consisting of wide field, Raman chemical imaging, multipoint, single point and line illumination.

* * * * *